United States Patent [19]

Wenzel et al.

[11] Patent Number: 4,893,631
[45] Date of Patent: Jan. 16, 1990

[54] ACTIVE ELEMENT SELECTION FOR CONTINUOUS BLOOD PRESSURE MONITOR TRANSDUCER

[75] Inventors: Dennis J. Wenzel; Dean C. Winter; Kevin S. Honeyager, all of San Antonio, Tex.

[73] Assignee: Colin Electronics Co., Ltd., Komaki, Japan

[21] Appl. No.: 160,146

[22] Filed: Feb. 25, 1988

[51] Int. Cl.$^4$ .............................................. A61B 5/02
[52] U.S. Cl. .................................... 128/672; 128/687
[58] Field of Search ........................ 128/672, 677–683, 128/687–690

[56] References Cited

U.S. PATENT DOCUMENTS

| | | | |
|---|---|---|---|
| 3,123,068 | 3/1964 | Bigliano | 128/672 |
| 3,219,035 | 11/1965 | Pressman et al. | 128/672 |
| 3,880,145 | 4/1975 | Blick | 128/672 |
| 4,423,738 | 1/1984 | Newgard | 128/672 |

Primary Examiner—Angela D. Sykes
Attorney, Agent, or Firm—Matthews & Branscomb

[57] ABSTRACT

A method for monitoring a transducer array of individual pressure or force sensitive elements and for selecting the element within the array which most tracks the actual pulse waveform in an underlying artery, thus providing the most accurate measurement of the patient's blood pressure. The outputs of all of the transducer elements are employed in locating the particular element which is centrally located over the artery. A limited number of elements exhibiting local minima of diastolic pressure is first chosen. Then, pulse amplitude outputs from the limited number of transducer elements are employed in selecting that element within the limited-number group which is to be used for obtaining blood pressure measurements. The method provided by the present invention selects from the limited-number group of elements that element about which is centered the greatest spatially weighted average of a predetermined number of pulse amplitude values.

8 Claims, 4 Drawing Sheets 4,893,631

ACTIVE ELEMENT SELECTION FOR CONTINUOUS BLOOD PRESSURE MONITOR TRANSDUCER

FIELD OF THE INVENTION

The present invention relates generally to the field of continuous noninvasive measurement of blood pressure. More specifically, the present invention provides a method and apparatus for monitoring a transducer array of individual pressure or force sensitive elements and for selecting the element within the array which most tracks the actual pulse waveform in an underlying artery, thus providing the most accurate mesurement of the patient's blood pressure.

BACKGROUND

There has been considerable interest in recent years in the development of a monitoring system for obtaining a continuous measurement of a patient's blood pressure. One of the most promising techniques for obtaining such a continuous measurement involves the use of an arterial tonometer comprising an array of small pressure sensing elements fabricated in a silicon "chip." The use of such an array of sensor elements for blood pressure measurements is disclosed generally in the following U.S. Patents: U.S. Pat. No. 3,123,068 to R.P. Bigliano, 3,219,035 to G. L. Pressman, P. M. Newgard and John J. Eige, 3,880,145 to E. F. Blick, 4,269,193 to Eckerle, and 4,423,738 to P.M. Newgard, and in an article by G. L. Pressman and P. M. Newgard entitled "A Transducer for the Continuous External Measurement of Arterial Blood Pressure" (IEEE Trans. Bio-Med. Elec., April 1963, pp. 73–81).

In a typical tonometric technique for monitoring blood pressure, a transducer which includes an array of pressure sensitive elements is positioned over a superficial artery, and a hold-down force is applied to the transducer so as to flatten the wall of the underlying artery without occluding the artery. The pressure sensitive elements in the array have at least one dimension smaller than the lumen of the underlying artery in which blood pressure is measured, and the transducer is positioned such that more than one of the individual pressure-sensitive elements is over at least a portion of the underlying artery. The output from one of the presure sensitive elements is selected for monitoring blood pressure. The element that is substantially centered over the artery has a signal output that provides an accurate measure of intraarterial blood pressure. However, for the other transducer elements, the signal outputs generally do not provide as accurate a measure of intraarterial blood pressure as the output from the centered element. Generally, the offset upon which systolic and diastolic pressures depend will not be measured accurately using transducer elements that are not centered over the artery. In some prior art arrangements the pressure sensitive element having the maximum pulse amplitude output is selected, and in other arragnements the elements having a local minimum of diastolic or systolic pressure which element is within substantially one artery diameter of the element which generates the waveform of maximum pulse amplitude is selected. The latter method is shown in the above-mentioned J. S. Eckerle Patent No. 4,269,193. the selection method disclosed in Patent No. 4,269,193 generally identifies the correct transducer element to be used. However, pressure readings provided by individual elements of a transducer array may not be perfectly accurate due to any number of factors. Even small errors in the pressure reading may result in the selection of an incorrect transducer element using the system disclosed in Patent No. 4,269,193, in which case the blodd pressure measurements are inaccurate. A method for determining the correct transducer element for measuring blood pressure is disclosed in copending application Ser. No. 927,843 assigned to SRI International. The method disclosed in present invention represents an improvement on the method disclosed in the above-referenced patent application.

SUMMARY OF THE INVENTION

The present invention relates to a blood pressure monitoring system employing a transducer which comprises an array of individual pressure sensitive elements, each of which elements have at least one dimension smaller than the lumen of the underlying artery in which blood pressure is measured. The elements are of sufficiently small size such that the array positioned so as to extend across the artery a plurality of elements are located over the artery. The outputs of all of the transducer elements are employed in locating the particular element which is centrally located over the artery. A limited number of elements exhibiting local minima of either diastolic or systolic pressure is first chosen. Then, pulse amplitude outputs from the limited number of transducer elements are employed in selecting that element within the limited-number group which is to be used for obtaining blood pressure measurements. The difference between the systolic and diastolic pressure values is defined herein as the pulse amplitude of the blood pressure waveform.

Theoretically, the graph of diastolic or systolic pressure versus transducer element exhibits two peaks corresponding to the transducer elements which overlie in two edges of the artery, since those elements are subject to bending forces produced by the natural stiffness of the artery. The centered element, on the other hand, is not subjected to these forces and only measures the fluid pressure within the artery. The centered element, therefore, always exhibits a local minimum in the diastolic or systolic pressure graph. Physical theory also dictates that a graph of pulse amplitude versus transducer element would exhibit a symmetrical distribution of values centered about, and having the greatest magnitude at, those elements directly overlying the flattened artery. The method provided by the present invention selects from the limited-number group of elements having local diastolic minima that element about which is centered the greatest spatially weighted average of a predetermined number of pulse amplitude values.

The method of the present invention also satisfactorily handles pressure versus transducer element curves which are not smooth due to noise or the physical configuration of the elements. For example, if adjacent elements are also separated longitudinally, and the plane in which the elements lie is not perfectly perpendicular to the force vectors exerted at the flattened artery wall, adjacent elements would sense slightly different pressure values. These artifical variations can produce local minima in the diastolic pressure versus transducer element curve which may not be distinguishable from the "true" minimum produced by the centered element. This problem is solved by choosing that element about which is centered the greatest spatially averaged pulse amplitude.

The method of the present invention also compensates for failure of one or more of the transducer elements. In particular, the element selection method of the present invention is capable of ignoring those elements which are detected to unusable and can still provide accurate pressure readings.

Finally, the method of the present invention incorporates pulse amplitude detection citeria which result in an error condition being reported unless the pulse amplitude exceeds a certain predetermined value. The pulse amplitude will be less than that value when the hold-down pressure is insufficient to flatten the artery.

DETAILED DESCRIPTION OF THE PREFERRED EMBODIMENT

Figure 1:
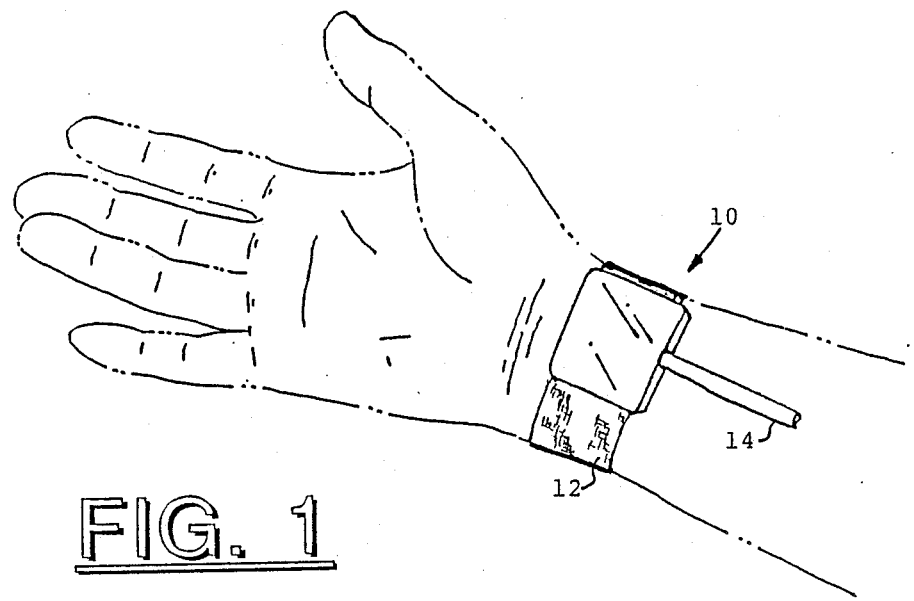
FIG. 1 is a view of the continuous blood pressure monitoring transducer of the present invention attached to a patient's wrist at a position overlying the radial artery.

Reference is now made to FIG. 1 wherein a continuous blood pressure monitor transducer 10 is shown attached to a patient's wrist a point overlying the radial artery. The transducer is attached by means of a strap 12 in a manner similar to a conventional wristwatch. A cable assembly 14 connected to the transducer contains electrical cables for carrying electrical signals to and from the transducer. The cable assembly 12 also contains a pneumatic tube for providing pressurized air to a pressurizable bladder in the interior of the transducer in order to bring a sensor into contact with the patient's skin in a manner described in greater detail hereinbelow.

For the transducer to properly measure blood pressure it is important that the underlying artery be partially compressed. Specifically, it is important that the artery be flattened by a plane surface so that the stresses developed in the arterial wall perpendicular to the face of the sensor are negligible. This generally requires that the blood pressure measurement be taken on a superficial artery which runs over bone, against which the artery can be flattened.

Figure 2:
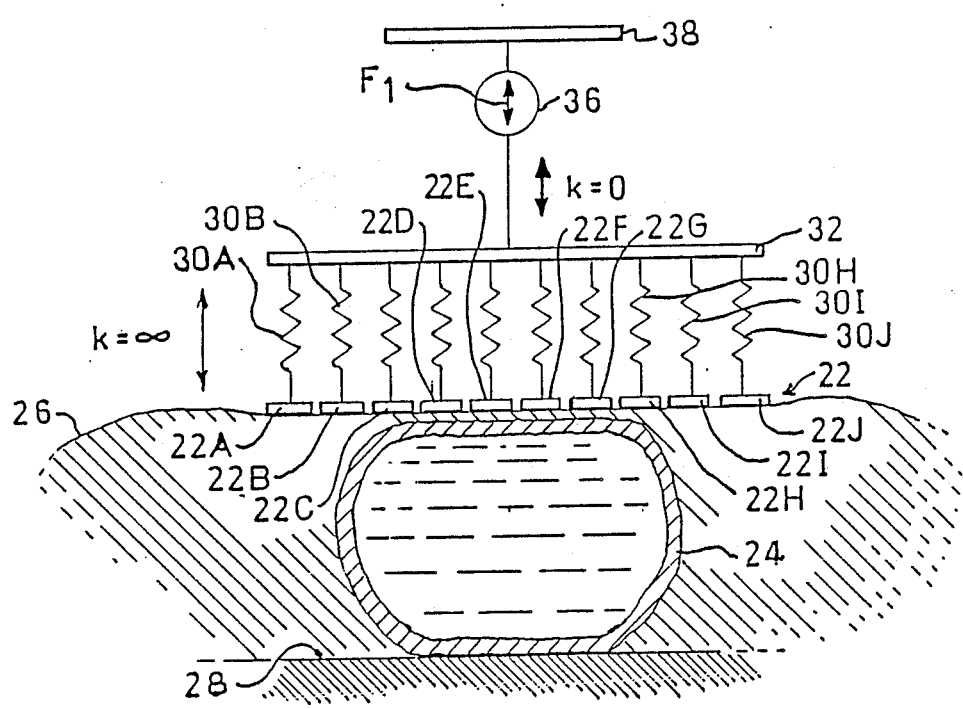
FIG. 2 is a schematic diagram illustrating the force balance between the artery and the multiple transducer elements (arterial riders), with the artery wall properly depressed to give accurate blood pressure readings.

Reference now is made to FIG. 2 wherein a diagrammatic mechanical model is shown which is representative of physical factors to be considered in blood pressure measurements using tonometry techniques. The illustrated model is adapted from that shown in the above-mentioned U.S. Pat. No. 4,269,193, issued to J. S. Eckerle, which by this reference is incorporated for all purposes. An array 22 of individual pressure sensitive elements or transducers 22-A through 22-E, which constitute the arterial riders, is positioned so that one or more of the riders are entirely over an artery 24. The individual riders 22-A through 22-E are small relative to the diameter of the artery 24, thus assuring that a plurality of the riders overlie the artery. The skin surface 26 and artery underlying the transducer must be flattened by application of a hold-down pressure to the transducer. One rider overlying the center of the artery is identified as the "centered" rider, from which rider pressure readings for monitoring blood pressure are obtained. Means for selecting the centered rider are discussed generally in the above mentioned U.S. Pat. No. 4,269,193. An improved method for locating the rider which best represents the actual waveform in the underlying artery is described in greater detail below. For present purposes it will be understood that one of the riders, such as rider 22-E, may be selected as the "centered" rider, in which case the remainder of the riders, here riders 22-A through 22-D and 22-F through 22-J, comprise "side plates" which serve to flatten the underlying skin and artery.

Superficial arteries, such as the radial artery, are supported from below by bone which, in FIG. 2, is illustrated by ground symbol 28 under the artery. The wall of artery 24 behaves substantially like a membrane in that it transmits tension forces but not bending moments. The artery wall responds to the loading force of the transducer array, and during blood pressure measurements acts as if it is resting on the firm base 28. With the illustrated system, the transducer assembly 10 and mounting strap 12, together with air pressure applied to a pressurizable bladder in the transducer assembly, supply the required compression force and hold the riders 22-A through 22-J in such a manner that arterial pressure changes are transferred to the riders which overlie the artery 24. This is illustrated schematically in FIG. 2 by showing the individual riders 22-A through 22-J backed by rider spring members 30-A through 30-J, respectively, a rigid spring backing plate 32, and hold-down force generator 36 between the backing plate 32 and the mounting strap system 38.

If, without force generator 36, the coupling between the mounting strap system 38 and spring backing plate 32 were infinitely stiff to restrain the riders 22-A through 22-J rigidly with respect to the bone structure 28, the riders would be maintained in a fixed position relative to the artery. In practice, however, such a system is not practical, and hold-down force generator 36, comprising (in the present example) a pneumatic loading system, is included to keep constant the force applied by the mounting strap system 38 to riders 22-A through 22-J. In the mechanical model the spring constant, k (force per unit of deflection) of the force generator, 36, is nearly zero. Pneumatic loading systems are shown and described in the above-referenced U.S. Pat. Nos. 3,219,035 and 4,269,193, and the Pressman and Newgard IEEE article. In addition, an improved pneumatic loading system is disclosed in a patent application entitled "Pressurization System for Continuous Blood Pressure Monitor T ransducer" filed on even date herewith.

In order to insure that the riders 22-A through 22-J flatten the artery and provide a true blood pressure measurement, they must be rigidly mounted to the backing plate 32. Hence, the rider springs 30-A through 30-J of the device ideally are infinitely rigid (spring constant $k = \infty$). It is found that as long as the system operates in such a manner that it can be simulated by rider springs 30-A through 30-J having a spring constant on the order of about ten times the corresponding constant for the artery-skin system, so that the deflection of riders 22-A through 22-J is small, a true blood pressure measurement may be obtained when the correct hold-down pressure is employed.

Figure 3:
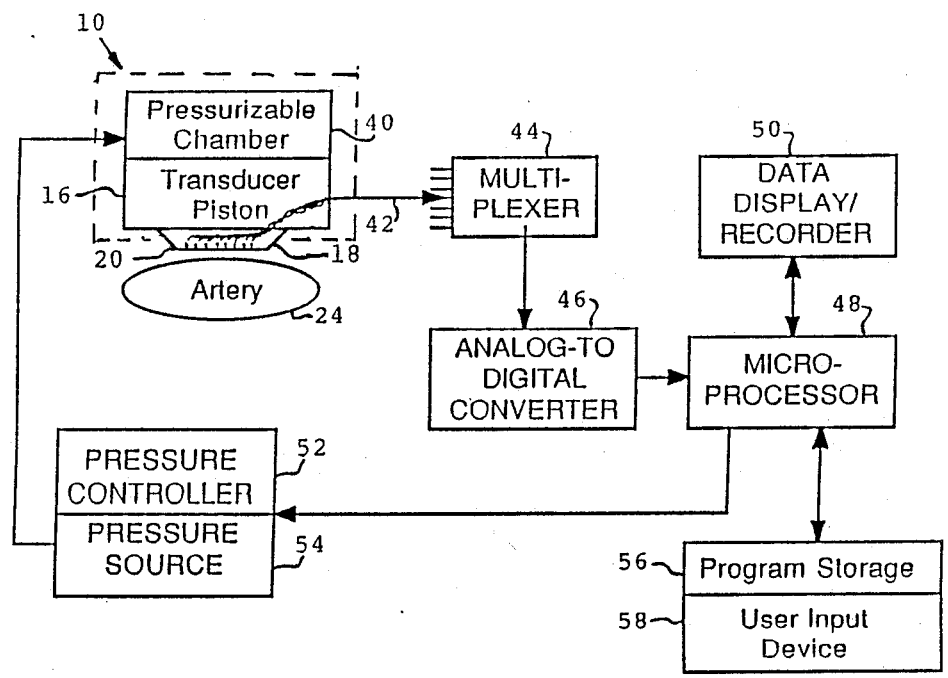
FIG. 3 is a simplified block diagram of the transducer assembly and associated system components for the continuous blood pressure monitoring system of the present invention.

Referring to FIG. 3, a simplified illustration of the transducer assembly 10 is shown to include a transducer piston 16, and a pressurizable chamber 40. The output of the individual pressure sensors (not shown) on the sensor 20 are connected by appropriate electrical wiring 42 to the input of a multiplexer 44. From the multiplexer, the signals are digitized by an analog-to-digital (A-D) converter 46, and the digitized signals are supplied to a microprocessor 48. Output from the microprocessor 38 is supplied to data display and recorder means 50 which may include a recorder, cathode ray tube montor, a solid state display, or an other suitable display device. Also, the output from the microprocessor is provided to the pressure controller 52 which controls a pressure source 54 to maintain the appropriate hold down pressure for the transducer piston 16. Operation of the microprocessor can be controlled by a program contained in program storage 56 or by user input from the user input device, which can be in the form of a keyboard or other interface device.

Figure 4:
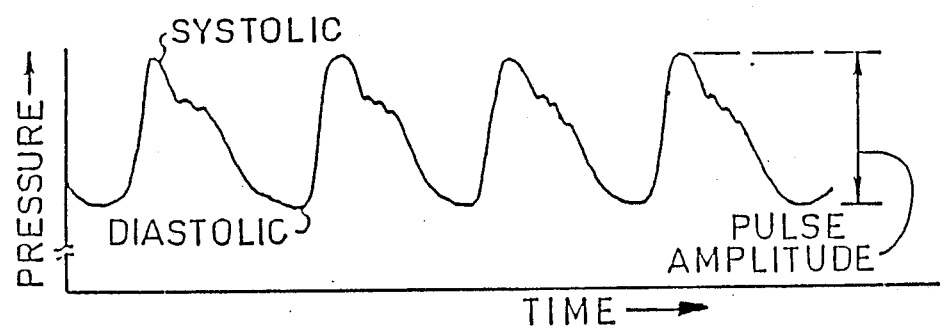
FIG. 4 is a waveform of human blood pressure versus time of the type which may be obtained using the present invention for illustrating systolic and diastolic pressures and pulse amplitude of the blood pressure wave.

Reference is now made to FIG. 4 which illustrates the signal waveform of the output from one of the pressure sensitive elements 22-A through 22-J which overlies artery 24. Other elements of the transducer aray which overlie the artery will have waveforms of similar shape. With a correct hold-down pressure and correct selection of the "centered" arterial rider (i.e., the rider substantially centered over the artery) the waveform is representative of the blood pressure within the underlying artery. Systolic, diastolic and pulse amplitude pressures are indicated on the waveform, wherein pulse amplitude is the difference between the systolic and diastolic pressures for a given heartbeat.

Figure 5A:
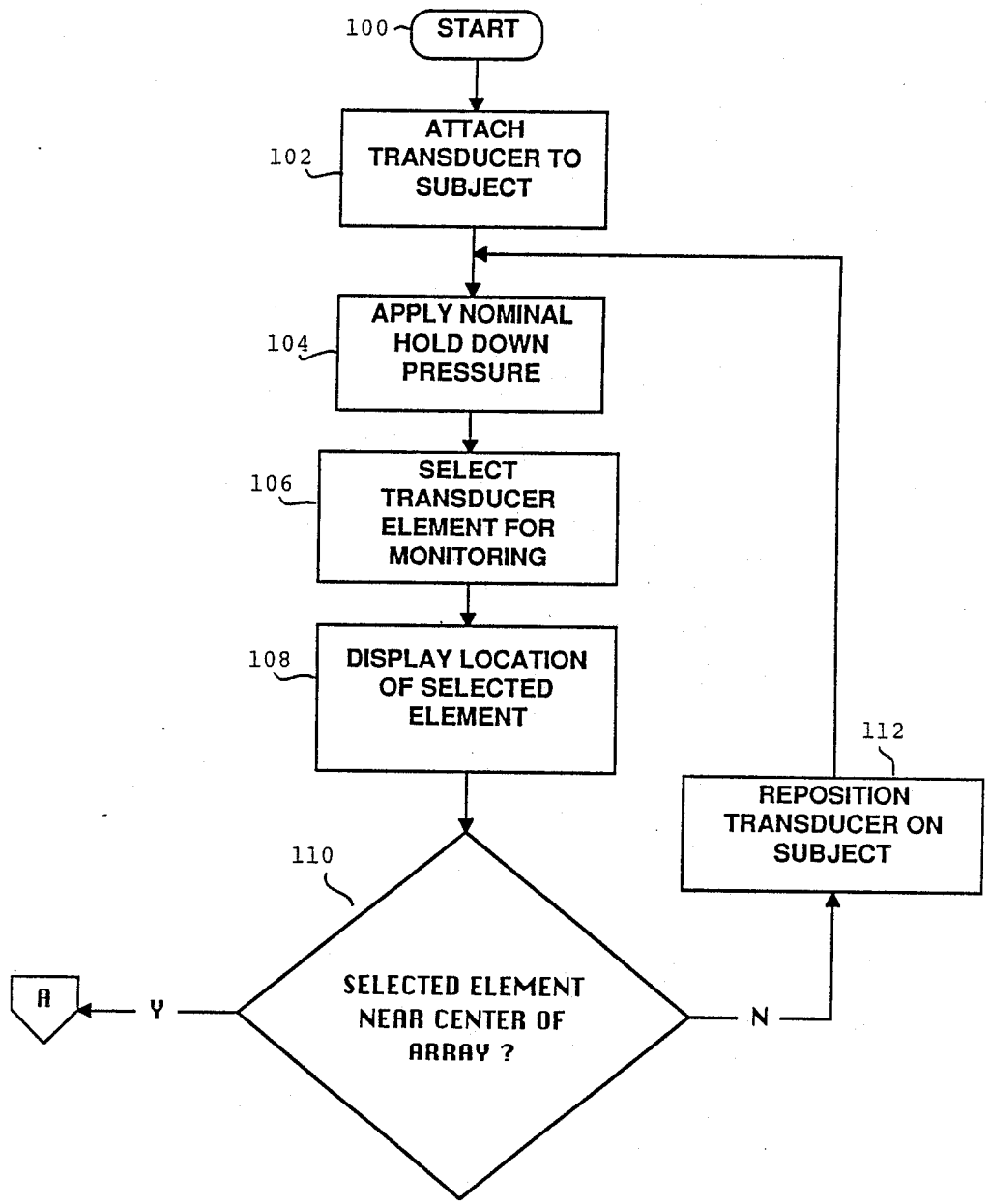
FIGS. 5A and 5B together show a flow chart for use in explaining overall operation of this invention.
Figure 5B:
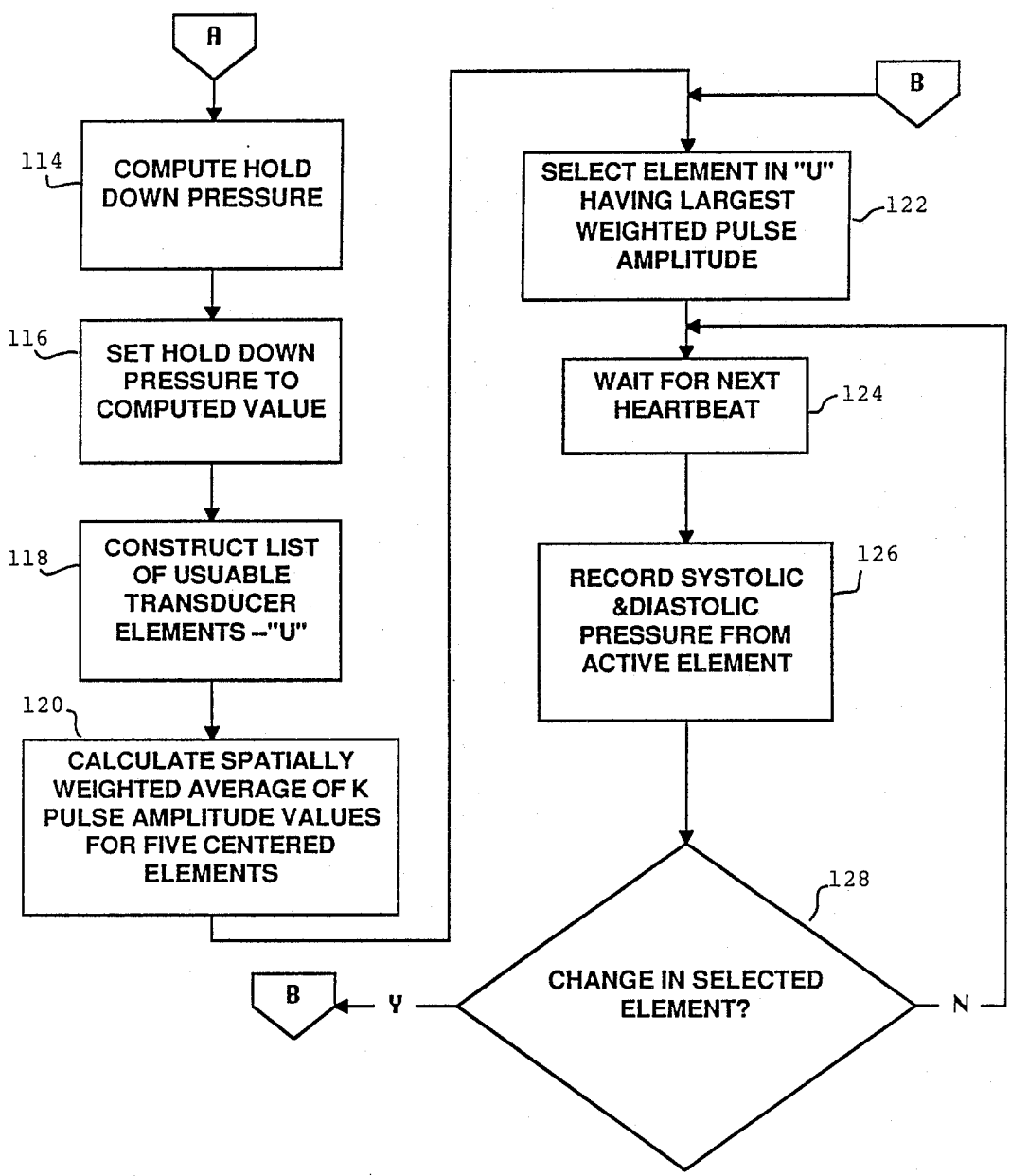

FIGS. 5a and 5b together show a flow chart of an algorithm for general overall operation of the blood pressure monitoring system. Some of the operations indicated therein are under control of the microprocess 48 responsive to programming instructions contained in program storage 56. Obviously, several program steps may be involved in the actual implementation of the indicated operations. Since the programming of such steps is well within the skill of the average programmer, a complete program listing is not required and is not included herein.

Preparation for monitoring is begun at START step 100 at which time system powder is turned on or a reset operation is performed by means not shown, and counters, registers, and timers in microprocessor 48 are initialized. The transducer is attached to the subject at step 102 at a location wherein at least one transducer element, such as element 22-E of transducer 22 should overlie the center of the artery 24. Next, at step 104, a nominal hold-down pressure (H-D.P.) is applied wherein air under pressure from source 54 is supplied to the transducer. For example, a hold-down pressure of 40 mmHg may be supplied to the transducer, which pressure serves to extend the transducer piston 16 outwardly a short distance from the bo ttom of the transducer case.

With the transducer attached to the subject, step 106 is entered wherein the transducer element to be used in monitoring blood pressure is selected. Novel algorithms which may be used in selecting the proper transducer element are described in detail hereinbelow. At step 108, the location of the selected element is displayed and in step 110 a decision is made to determine whether the selected element is near the center of the transducer array 22. If the selected element is not near the center of the array, step 112 is entered wherein the transducer is repositioned on the subject and step 1-4 through 110 are reentered. If the determination of step 110 indicates that the selected element is near the center of the transducer array, then step 114 is entered wherein the optimal hold down pressure is computed. Novel means for determining the optimum holddown pressure are described in a patent application entitled "Pressure Control System for Continuous Blood Pressure Monitor Transducer," filed on even date herewith. In step 116, the computed hold-down pressure is set by control of pressure controler 54 by the microprocessor 48. With the transducer properly positioned on the subject and the correct holddown pressure supplied thereto, the system is in condition for obtaining accurate blood pressure readings.

At step 118, the set of usable transducer elements U is determined by the system. This is accomplished from either operator input or by the system receiving an out-of-range output from one of the elements. From the set U of usable elements, the differences in diastolic pressure between each element and its immediately adjacent neighbor are calculated as follows:

$$\text{diff}_0 = d_1 - d_0$$
$$\text{diff}_1 = d_2 - d_1$$
$$\vdots$$
$$\text{diff}_{i-1} = d_{i+1} - d_{i-1}$$
$$\vdots$$
$$\text{diff}_{i+1} = d_{i+2} - d_{i+1}$$

where $d_n$ is the diastolic pressure measured by the transducer element n. Next those transducer elements exhibiting a local minimum of diastolic pressure are grouped into a set L. Set L is generated by selecting those elements n for which $\text{diff}_{n-1}$ is negative and $\text{diff}_n$ is positive. These elements then correspond to regions on the diastolic pressure versus transducer element waveform negative-to-positive slope changes, referred to herein as local minima. An odd-integer k, corresponding to the minimum number of transducer elements which spans one artery diameter, is then generated. For each element $E_n$ in L, a spatially weighted average of k pulse amplitude values from k transducer elements centered about element n is calculated, using $\text{Wavg}_n$. $\text{Wavg}_n$ is calculated at step 120 by first multiplying each pulse amplitude $p_i$ from element $E_i$ by a weighting factor $W_i$. $W_i$ is calculated a $(k+1)/2$ when $i=n$, where $E_n$ is the element about the average is to be centered, and decrements by one sequentially for each element on either side of $E_n$. For example, if $K=5$ and $n=7$:

$$W_7 = (k+1)/2 = 3$$
$$W_6 = W_8 = 2$$
$$W_5 = W_9 = 1$$

Next a sum is calculated of the products of each pressure $p_i$ times it weighting factor $W_i$, and this sum is divided by the sum of the weighting factors, i.e., $W_{n-[(k-1)/2]} + \ldots + W_n + \ldots + W_{n+[(k-1)/2]}$. Thus, $$Wavg_n = \frac{\Sigma W_i p_i}{\Sigma W_i}$$

where i varies from $n-[k-1)/2$ to $n+](k-1)/2]$ over both summations.

When elements $E_i$ are either unusable or do not physically exist, $W_i$ in the formula above is assigned a value of zero. for example, assuming k=5 and n=7, and that element $E_5$ does not exist:

$$Wavg_7 = \frac{0 + 2p_6 + 3p_7 + 2p_8 + p_9}{0 + 2 + 3 + 2 + 1}$$

If, on the other hand, $E_6$ was unusable, the resulting value of Wavg7 would be calculated as:

$$Wavg_7 = \frac{p_5 + 0 + 3p_7 + 2p_8 + p_9}{1 + 0 + 3 + 2 + 1}$$

From the set L, the element $E_i$ having the largest spatially weighted pulse amplitude average centered about it is selected as the measuring transducer element at step 122. With the correct pressure transducer element selected, step 124 is entered wherein the system waits for the next heartbeat. From the output of the selected transducer element, systolic and diastolic pressure values together with pulse amplitude values are readily determined in step 126. Also, pulse rate is readily calculated by determining the time between successive diastolic or systolic pressures. At step 126, values calculated and determined in step 124 are displayed and/or recorder along with the actual waveform.

After the values identified in step 126, such as systolic and/or diastolic pressure, are displayed, decision step 126 is entered wherein the system determines whether there has been a change in the selected element. Such a change can be related to a number factors, including detection of motion in the patient's wrist or repositioning of the transducer on the patient's wrist. If no such change has been indicated, step 124 is reentered wherein the system waits for the next heartbeat. However, if such a request for recomputation has been received, then the system returns to step 122, as shown in FIG. 5b.

Although the method and apparatus of the present invention has been described in connection with the preferred embodiment, it is not intended to be limited to the specific form set forth herein, but on the contrary, it is intended to cover alternatives and equivalents as may reasonable be included within the spirit and scope of the invention as defined by appended claims.

I claim:

1. A system for the continuous external measurement of blood pressure in an underlying artery of a subject, including an array of individual pressure sensitive elements, the length of which array exceeds the diameter of the underlying artery, comprising means for selecting an ordered set Q which includes of said elements ordered with respect to their physical position;

means for selecting a set L of those elements having local minima on a plot of diastolic or systolic pressure versus transducer element number;

means for computing a spatially weighted average of pulse amplitude values from the set Q centered about each element of set L;

means for specifying the number of elements over which said spatially weighted average of pulse amplitude values is to be computed; and means for operatively selecting the output of the element from set L which has the largest spatially weighted average of pulse amplitude values centered about it as the single measurement to represent the blood pressure existing in said underlying artery.

2. The system according to claim 1, further comprising means for eliminating those elements determined to be inoperative or non-existent from the set Q, designated as the set U.

3. The system according to claim 2 wherein the means for computing a spatially weighted average of pulse amplitude values centered about each element of set L comprises calculating the spatially weighted average, $Wavg_n$, where n is the element number from set L about which the spatially weighted average is to be taken, according to the formula:

$$Wavg_n = \frac{\Sigma W_i p_i}{\Sigma W_i}$$

where $W_i$ is a weighting factor for the ith element in set U, $p_i$ is the measured pulse amplitude at the ith element, and i varies from $n-[(k-1)2]$ to $n+[(k-192]$ where k repesents an odd integral number of elements over which the spatial average is to be taken.

4. The system according to claim 3, wherein k is chosen to be the smallest odd integral number of elements which completely span the most probable diameter of the subject's underlying artery.

5. The system according to claim 4, wherein $W_i$ is calculated to be $(k+1)/2$ where i=n and where the spatial average is to be centered about the nth element of set L and where each $W_i$ is equal to $W_n$ decremented by the absolute value of i minus n.

6. The system according to claim 5, wherein Wi is set to zero for each i for which the ith element of set Q is not a member of set U.

7. The system according to claim 2, wherein the set L is chosen from the set U.

8. The system according to claim 7, wherein the means for selecting set L comprises:

means for computing for each element in the set U the differences between the pulse amplitude of that element and the pulse amplitude of the two elements most physically adjacent;

means for selecting those elements of set U having pulse amplitudes less than either of the two elements most physically adjacent.

* * * * *